(12) United States Patent
Melman et al.

(10) Patent No.: US 6,728,429 B1
(45) Date of Patent: Apr. 27, 2004

(54) OPTICAL DETECTION

(75) Inventors: Paul Melman, Newton, MA (US); Shmuel Halevi, Chestnut Hill, MA (US)

(73) Assignee: BioTell, Inc., Brookline, MA (US)

( * ) Notice: Subject to any disclaimer, the term of this patent is extended or adjusted under 35 U.S.C. 154(b) by 419 days.

(21) Appl. No.: 09/785,762

(22) Filed: Feb. 16, 2001

Related U.S. Application Data
(60) Provisional application No. 60/183,011, filed on Feb. 16, 2000.

(51) Int. Cl.$^7$ ............................ G01N 21/17; G02B 6/00
(52) U.S. Cl. ............................ 385/12; 385/40; 356/445; 422/82.11
(58) Field of Search ................... 385/12, 40; 422/82.11; 356/244, 445

(56) References Cited

U.S. PATENT DOCUMENTS

| | | | |
|---|---|---|---|
| 3,934,061 A | 1/1976 | Keck et al. | 427/165 |
| 4,673,475 A | 6/1987 | Windischmann | 204/192.11 |
| 4,889,427 A | 12/1989 | Van Veen et al. | 356/445 |
| 4,949,350 A | 8/1990 | Jewell et al. | 372/45 |
| 5,023,053 A | 6/1991 | Finlan | 422/82.05 |
| 5,055,265 A | 10/1991 | Finlan | 422/82.05 |
| 5,064,619 A | 11/1991 | Finlan | 422/82.05 |
| 5,242,828 A | 9/1993 | Bergström et al. | 435/291 |
| 5,313,264 A | 5/1994 | Ivarsson et al. | 356/73 |
| 5,359,681 A | 10/1994 | Jorgenson et al. | 385/12 |
| 5,395,587 A | 3/1995 | Brigham-Burke et al. | 422/68.1 |
| 5,485,277 A | 1/1996 | Foster | 356/445 |
| 5,492,840 A | 2/1996 | Malmqvist et al. | 436/518 |
| 5,561,069 A | 10/1996 | Brigham-Burke et al. | 436/518 |
| 5,620,850 A | 4/1997 | Bamdad et al. | 530/300 |
| 5,814,565 A | 9/1998 | Reichert et al. | 422/82.11 |
| 5,815,278 A | 9/1998 | Johnston et al. | 356/445 |
| 5,991,488 A | 11/1999 | Salamon et al. | 385/129 |
| 6,007,690 A | 12/1999 | Nelson et al. | 204/601 |
| 6,111,652 A | 8/2000 | Melendez et al. | 356/445 |
| 6,127,129 A | 10/2000 | Corn et al. | 435/6 |
| 6,127,183 A | 10/2000 | Ivarsson et al. | 436/34 |
| 6,373,577 B1 * | 4/2002 | Brauer et al. | 356/445 |
| 6,432,364 B1 * | 8/2002 | Negami et al. | 422/82.11 |

OTHER PUBLICATIONS

"Waveguide surface plasmon resonance sensors" by R.D. Harris and J.S. Wilkinson, Sensors and Actuators B, vol. 29, pp. 261–267, Elsevier Science S.A., 1995.

(List continued on next page.)

*Primary Examiner*—Akm Enayet Ullah
*Assistant Examiner*—Jerry T Rahll
(74) *Attorney, Agent, or Firm*—Fish & Richardson P.C.

(57) ABSTRACT

The invention features a waveguide based devices, methods, and systems to increase sensitivity of surface plasmon resonance (SPR) measurement through the use of differential detection. The enhanced sensitivity enables analysis and detection of a wide range of analytes including, for example, DNA, antibodies, proteins, and other chemical compounds. These methods achieve this result by sampling the SPR response curve at more than one point. This can be achieved using a detection device with sets of optical waveguides having distinct propagation parameters, or by using light of different wavelengths. These methods are suitable for multi-analyte and multi-sample applications in a miniaturized detection system. Furthermore, this invention makes use of an alternating polarity electric field to reduce nonspecific analyte binding and detection time.

28 Claims, 4 Drawing Sheets

OTHER PUBLICATIONS

Fiber Optic Sensors http://dvorak.mse.vt.edu/faculty/hendricks/mse4206/projects98/group07/fiber.htm.

Typical SPR Sensor Chip http://dvorak.mse.vt.edu/faculty/hendricks/mse4206/projects98/group07/prism.htm.

How Drugs are Discovered http://dvorak.mse.vt.edu/faculty/hendricks/mse4206/projects98/group07/drugs.htm.

Surface Plasmon Resonance http://dvorak.mse.vt.edu/faculty/hendricks/mse4206/projects98/group07/physics.htm.

Biological Targets and Receptors http://dvorak.mse.vt.edu/faculty/hendricks/mse4206/projects98/group07/receptors.htm.

Surface Plasmon Resonance http://www.cranfield.ac.uk/biotech/spr.htm.

Surface Plasmon Resonance Biosensors http://www.biosensor.com/bio/plasm.htm.

Quantech Home http://www.quantechltd.com/Content/Default.asp.

DNA Microarray —A technology that is reshaping molecular biology http://www.gene–chips.com.

Surface Plasmon Resonance http://www.cpac.washington.edu/~campbell/projects/spr.html.

* cited by examiner

OPTICAL DETECTION

CROSS-REFERENCE TO RELATED APPLICATION

This application claims priority under 35 USC §119(e) to U.S. Provisional Application Serial No. 60/183,011, filed on Feb. 16, 2000, the entire contents of which are hereby incorporated by reference.

TECHNICAL FIELD

This invention relates to optical detection of analytes, and more particularly to detection of biological, biochemical, and chemical substances using surface plasmon resonance.

BACKGROUND

Surface plasmon resonance (SPR), the resonant transfer of electromagnetic energy from the evanescent field of a light beam into electron-photon coupled oscillation in some metals, has been used extensively in sensor applications. The magnitude of this resonant phenomenon depends critically on equalizing the phase velocity of excitation beam with that of the surface plasmon wave (SPW), whose propagation velocity strongly depends on the index of refraction of the medium in close proximity to the metal surface. To achieve this equality, the propagation velocity of the electromagnetic wave needs to be reduced. A number of techniques have been used. For example, a conventional SPR spectroscopic device, consisting of a metallic film used with a prism to provide a surface plasmon wave, can be modified by coating the film with a dielectric layer. See, e.g., U.S. Pat. No. 5,991,488.

The most widely deployed technique for SPR detection uses a prism to generate total internal reflection at one of its surfaces. This surface is coated with a thin metallic film, which supports a SPW. See, e.g., U.S. Pat. Nos. 5,991,488; 4,889,427. Changes in the incident light angle, or its wavelength, produce changes in propagation velocity along the prism surface and thus strongly affect the amplitude of the reflected light. The change of the index of refraction at the surface changes the angle at which the resonance occurs. This principle is used in analysis and detection of samples containing analyte. The prism surface is pre-coated with an immobilized layer of a ligand, which has a strong affinity for a analyte, causing the analyte to bind to the surface and thus modify its index of refraction. This modification shifts the SPR curve, i.e., the light intensity versus velocity mismatch, and affects the output light intensity, which is a measure of binding.

Most devices calculate a change in the plasmon resonance angle. See, e.g., U.S. Pat. No. 4,889,427. However, this approach requires a very stable mechanical structure to achieve the requisite sensitivity. The instruments using this approach are large, sensitive to temperature, immobile, and expensive. Furthermore, due to free beam reflection at the surface, it is difficult to expand their operation to more than a few independent sensing channels. Other configurations include the use of waveguides such as optical fibers or planar, single mode structures, designed to detect a shift of the SPR response curve, which measures a change in the index of refraction of the metallic film-abutting layer. See, e.g., U.S. Pat. Nos. 5,815,278; 5,485,277; and 5,359,681. In the case of optical fibers, the wavelength of light can be changed to trace out the SPR response curve.

Single planar waveguides can be used to detect changes in transmitted light intensity, but they lack a free parameter (such as angle) to trace out the response curve. Thus, any spurious change in transmitted light cannot be distinguished from a real signal. Some planar devices include a reference waveguide having a deactivated ligand layer. See U.S. Pat. No. 5,485,277. While this reference controls for mechanical instabilities and nonspecific binding effects but requires a deactivation step and does not account for differences between the deactivated and activated ligand layers.

SUMMARY

The invention features a differential mode of detection using surface plasmon resonance (SPR) measurement that avoids mechanical and optical instabilities and enhances detection of analytes including, for example, DNA, antibodies, proteins, and chemical compounds. The invention achieves these results by using sets of optical waveguides having different propagation parameters, or light of different wavelengths, and is suitable for multi-sample and multi-analyte applications in a miniaturized detection system. Furthermore, the invention can include the use of an alternating electric field to reduce nonspecific analyte binding and detection time.

The new detection devices can have one or more sets of two or more waveguides, metallic films (e.g., gold or silver) that support a surface plasmon wave covering at least a portion of each of the waveguides, and ligand layers for binding analytes to the metallic films. The waveguides can be made on a substrate or in optical fibers, wherein the substrate comprises a first material, which can be an optically transparent material (e.g., borosilicate, silicon dioxide or a polymer) with top and bottom surfaces, The top surface is covered by a second material, e.g., magnesium fluoride, having an index of refraction lower than the index of refraction of the first material. The metallic film can cover a portion or the entire length of the waveguides.

In another embodiment of these detection devices, each waveguide in a set on the detection device has a distinct light propagation velocity. To provide this distinct light propagation velocity, each waveguide in a set can have a distinct size or shape (e.g., a distinct width) or be covered by a second material with a distinct thickness.

New methods of differential SPR detection involve transmitting multiple light beams through at least one waveguide on a detection device, where the beams of electromagnetic radiation, i.e., light beams, have different light propagation velocities within the waveguides. The detection device has metallic film that supports a surface plasmon wave and at least in part covers the waveguides. The intensities of the transmitted beams are measured, and a difference between intensities for one or more sets of waveguides are calculated at a first time. A sample, e.g., a liquid or gas, is provided to the metallic film, and a second difference is calculated for the two light beams at a second time. These differences are compared to detect any shift of the SPR curve.

The metallic film can have ligand layers for binding analytes. The two light beams can be light beams with different wavelengths and these light beams can be transmitted through the same waveguide. The two light beams can also be two light beams transmitted through two waveguides having distinct light propagation velocities (i.e., waveguides having distinct shape or size, e.g., distinct widths). Alternatively, where the detection device involves waveguides on a substrate that has a first material with top and bottom surfaces covered by a second material on its top surface that has a lower index of refraction than the first material, the two light beams can be transmitted through two waveguides covered by distinct thicknesses of the second material. The methods can repeat the steps of obtaining a second difference and comparing it to the first difference either continuously or at intervals.

Furthermore, the methods can include providing an alternating polarity electric field to the sample, where the electric field has a field strength less than a binding strength between the ligand layer and the analytes. In another implementation, the methods can involve providing an alternating polarity electric field to the sample, where the electric field has a greater strength during the part of its cycle that causes binding of the analytes than the strength during the part of its cycle that causes unbinding of the analytes.

Detection systems include a cell containing one or more samples that provide the sample to contact at least one metallic film that supports a surface plasmon wave and covers at least a portion of one or more waveguides, at least one light source (i.e., a laser, e.g., semiconductor laser, or laser diode) to transmit light beams into the waveguides, a photodetector to convert the transmitted light into electrical signals, and a processor, e.g. a differential amplifier, to provide results. The processor converts the electrical signals into measured intensities and then computes a first difference between measured intensities for a pair light beams at a first time and a second calculated difference at a later time. Comparing the first difference and the second difference indicates any shift of the SPR curve, and this process can be repeated continuously or at intervals.

The cell can include one or more conduits to flow the sample over ligand layers attached to the metallic films for analyte detection. A differential amplifier or a handheld, mobile, personal, or mainframe computer can be used as a processor. In addition, results can be provided, e.g., in digital, electronic form, to locations physically separated from the sources and detectors by, e.g., satellite, radiofrequency broadcast, fiber optic cable, or electric wire. The detection systems itself can further include a source of voltage connected through wires to physically separated conductive pads, which can include the metallic film, within the cell to provide an electric field across a separation.

A ligand layer is a collection of binding moieties attached to the metallic film either directly or using an intermediary.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The devices, methods, and systems of differential SPR detection offer numerous advantageous in diverse contexts. They can be used to detect a change in a sample property, e.g., a temperature-induced change in viscosity, or a ligand-analyte interaction. They are suitable for laboratory use in both clinical and research settings. In a clinical setting, systems featuring differential SPR detection can enhance efficiency by analyzing a number of samples simultaneously for multiple analytes, with little effort required from the laboratory technician. In a research setting, the ability to study binding kinetics by collecting time-series data is particularly useful. Differential SPR detection can also be used in the home or office, since the devices are easy to use, portable, and inexpensive. The robustness of these systems avoids mechanical and optical instabilities, as well as the lack of human intervention required to maintain them, make them ideal for use in the field. In particular, configuring these SPR systems for communication of results to remote locations is especially attractive as it reduces communication time, transmission errors, and the need for the observer to be physically present at the location where the detection device is being used.

Other features, objects, and advantages of the invention will be apparent from the description and drawings, and from the claims.

DESCRIPTION OF DRAWINGS

Like reference symbols in the various drawings indicate like elements.

DETAILED DESCRIPTION

The invention is based on the discovery that, using a differential mode of SPR detection, one can avoid mechanical and optical instabilities in the detection apparatus and increase sensitivity. Differential detection can be accomplished by varying propagation parameters within a set of waveguides on a detection device or by varying the wavelength of the transmitted radiation. Changes in the bulk refractive indices of samples can be detected, in addition to detection of ligand-analyte interactions. Detection of numerous biological, biochemical, and chemical analytes is achieved by varying the components of the ligand layer. Classes of possible analytes include, e.g., DNA, antibodies, proteins, lipids, and other chemical compounds. The new SPR system can be used to measure thermodynamic effects or, by calculating results at multiple points in time, can be employed in kinetic analysis. Using multiple sets of waveguides and conduits for analyte samples, the new methods and systems enable multi-sample, e.g., multi-solution, and multi-analyte analysis. The methods and systems also feature use of an alternating electric field to inhibit nonspecific binding, enhance specific binding and reduce detection time. By damping the field strength during the portion of the cycle that causes unbinding, specific binding can be further improved.

Detection Devices

Detection devices for applying the new differential detection methods can use any form of waveguide, i.e. a planar waveguide or an optical fiber. Chips provide a cost-effective means of using the new differential detection methods that benefit from ease of use and manufacture. Appropriate chips, such as those diagrammed in FIGS. 1 and 2, can be manufactured using known photolithography techniques. Single mode or multimode waveguides 11 can be formed by standard techniques, e.g., by using plasma enhanced chemical vapor deposition (PECVD), to deposit a second material 12 on a first material 10 and lithographic etching using a photoresist. See, e.g., U.S. Pat. No. 5,814,565. Simple ion exchange methods can also be used for waveguide fabrication. See, e.g., R. D. Harris et al., Sensors and Actuators B, 29:261, 1995. The second material 12, which is deposited on top of the first material 10, is selected such that its index of refraction is less than that of the first material. The first material 10 can be an optically transparent material such as silicon dioxide (e.g., glass, natural quartz, fused silica), borosilicate, or a polymer, and the second material 12 can be a dielectric material, such as magnesium fluoride, a low index oxide, or a polymer. See, e.g., U.S. Pat. No. 5,814,565; W. J. H. Bender et al., Analytical Chemistry, 66:963, 1994. A suitable wafer can be a glass slide or chip that is, e.g., 0.5 mm thick and 125 mm wide, e.g., in diameter.

Figure 1:
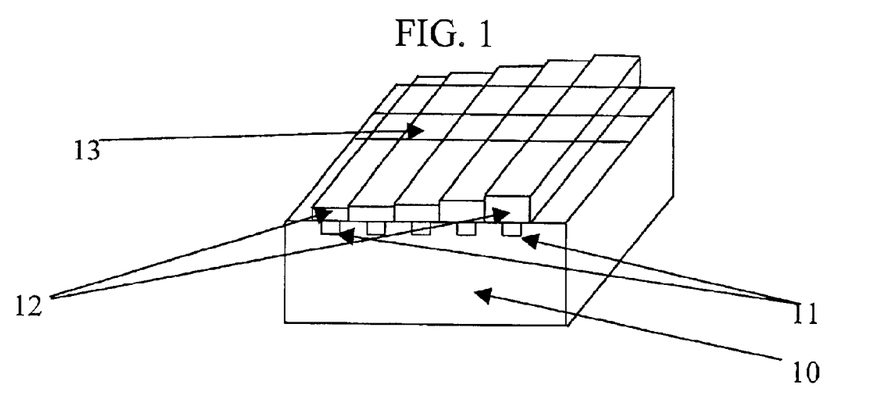
FIG. 1 is a diagram of a detection device with waveguides having distinct light propagation velocities due to varied thicknesses of a second material over a first material containing the waveguides.
Figure 2:
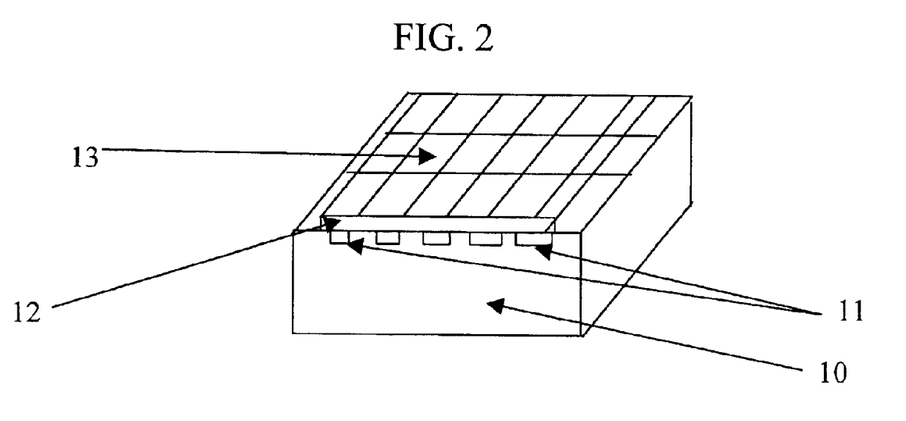
FIG. 2 is a diagram of a detection device with waveguides having variable width.

The new methods involve varying the propagation of light through the waveguides to sample the SPR curve differentially. One way this can be accomplished is by varying the optical parameters of the waveguides themselves. A means of varying the optical parameters of the waveguides is to use different thicknesses of the second material 12, as shown in FIG. 1. Another approach is to use waveguides of different sizes or shapes. FIG. 2 shows a detection device having waveguides 11 with different widths.

To use the waveguides in SPR detection, a metallic film 13, e.g., silver, gold copper, aluminum, platinum, nickel, cobalt, chromium, vanadium, tungsten, or a semiconductor, that supports a SPW covers at least a portion of each waveguide. This metallic film 13 can be a strip that spans the entire detection device, as in FIGS. 1, 2, 4, and 5, or individual pads over one or more waveguides, as in FIGS. 6, 7, and 8. The film can be deposited using known techniques, e.g., electron beam deposition, vapor phase deposition, or sputtering. See, e.g., U.S. Pat. No 4,673,475. For example, a 99.99% pure gold layer can be deposited on a glass wafer that has been previously cleaned, e.g., using samples of potassium hydroxide, ammonia, and sulfuric acid.

A ligand layer for binding analytes is formed on the metallic film using known chemistry. See, e.g., U.S. Pat. Nos. 5,620,850 and 5,242,828. For example, ligands can be attached using sulfide bonds as described in, e.g., U.S. Pat. No. 5,242,828. The ligand layer can be formed using an intermediary layer, e.g., an avidin layer, that binds the ligand layer, e.g., a biotinylated layer, to the metallic film. Another intermediary uses thiol chemistry; 16-mercapto-1-hexadecanol forms a sulfide bond with the gold at one end of the compound and provides a site for covalent bonding at the other. A layer of dextran hydrogel with receptor groups can be conveniently bonded to this intermediary layer to provide a ligand layer for binding analytes.

Suitable ligands include biological, biochemical, and chemical moieties. They can be hydrophobic or hydrophilic, charged or neutral, small or large. Ligands can be, e.g., DNA, antibodies, proteins, lipids, or chemical compounds. Complementary DNA can be used, for example, to detect viroids or genetic mutations. Among others, antibodies in the ligand layer can be IgD, IgM, IgG, IgA, and IgE. Proteins can be used to detect the presence of a substrate, e.g., another protein or a nucleic acid. Drugs or drug targets are examples of chemical compounds that can be used as ligands. A tremendous variety of ligands can be used because the SPR effects of binding are not chemically dependent, allowing the detection devices to be used for detecting a diverse group of analytes.

Figure 4:
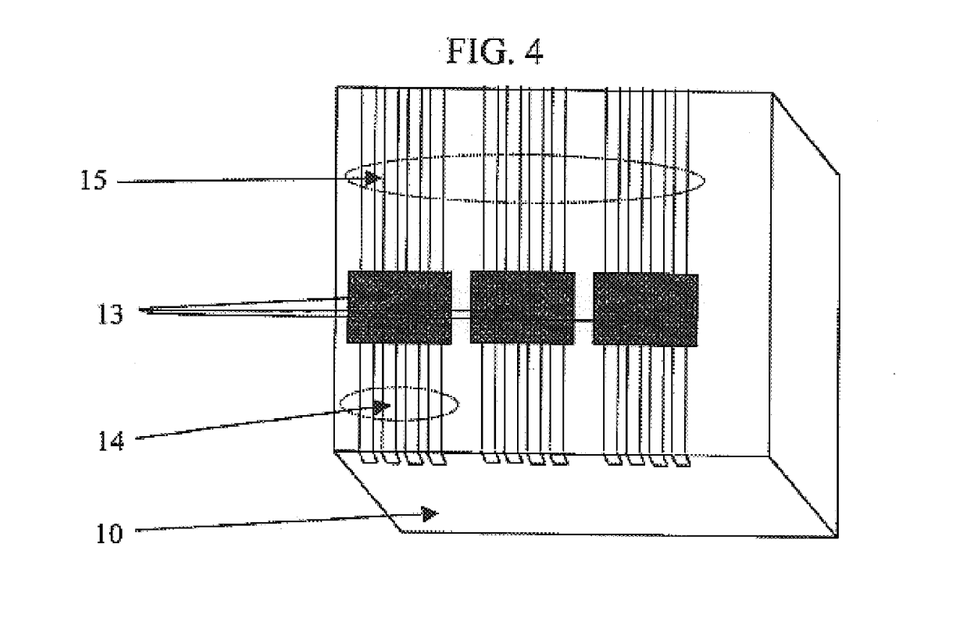
FIG. 4 is a diagram of a device for detection using multiple ligands.

Detection devices can be designed with a single set of waveguides and a single ligand or can have multiple sets of waveguides and provide a multi-analyte detection system. A detection device using multiple ligands is shown in FIG. 4. Where differential detection is accomplished by using waveguides having different light propagation velocities, a set of at least two waveguides is required. Increasing the number of waveguides in a set provides greater sensitivity, and the number of waveguides is only limited by the size of the detection device. Sets of two, three, four, five, six, seven, eight, or even more waveguides can be used depending on the sensitivity sought. Sensitivity increases as the number of waveguides in a set increases because the SPR response curve is sampled at more points, permitting shifts in the curve to be more readily measured. FIG. 4 shows a set of four waveguides 14 for detecting analyte binding to a particular ligand. Together, all the sets of waveguides 15 provide a multi-analyte detection system on a detection device.

Optical fibers can also constitute the sets of waveguides. A metallic film can be deposited on a length of the fiber core that is not covered by cladding. One approach is to overcoat a fiber core with a material having a lower index of refraction than the core, followed by deposition of a metallic film, e.g., gold film, that supports a SPW on the surface of that material. Cladding can be provided to the surfaces of the core not covered with gold. Alternatively, cladding can be selectively stripped from a fiber core, e.g., by hydrofluoric acid etching or polishing, to provide sites for deposition of the low index layer and metallic film. Using either approach, ligands can than be bound to the gold surfaces. This structure is equivalent to a single planar waveguide described above. Multiple fibers can be collected in a bundle by, e.g., placing them in precision v-grooves in a holder. The light propagation velocities within the optical fibers can be varied by composing the fiber cores of materials having distinct refractive indices or varying their size or shape. In particular, one can vary the diameter of the waveguides. Using fibers, the length of the detection device can be easily increased to considerable distances, and an apparatus for bundling the fibers can be provided only in the region of ligand-analyte interaction.

General Methodology

The invention also features new methods for differential SPR detection. These methods involve transmitting light beams through one or more waveguides on a detection device and measuring the transmitted light. To implement the differential detection methods, the difference between the intensities of a two light beams is calculated at a first, or initial, time. The first calculated difference obtained at this first time provides a baseline to which each further difference, i.e., a second calculated difference, obtained at a later time, i.e., a second time, can be compared. By providing one or more different analytes in sample over the ligand layers, one can shift an SPR response curve and therefore the intensity of the light beams transmitted through the waveguides. This shift of the SPR response curve occurs as a result of changing the index of refraction of the metallic film. The difference between the first and second calculated differences that reflects the effects of any analyte binding that has occurred between the baseline difference and any second calculated difference obtained thereafter. Since measurements are of an optical parameter of the system, this detection scheme is independent of the ligand-analyte binding chemistry.

Figure 3:
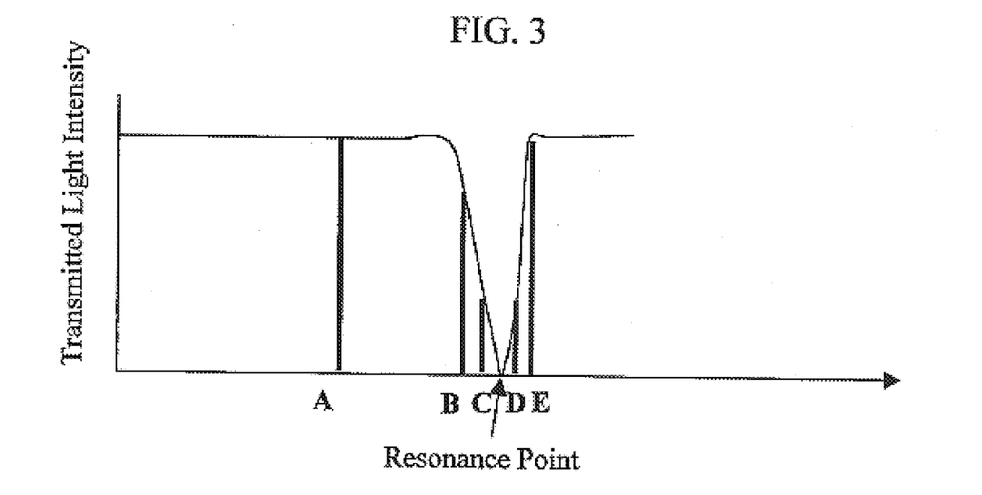
FIG. 3 is a graph of a surface plasmon response curve.

This differential mode of detection, where a first calculated difference is compared to a second calculated difference to reveal any shift of the SPR curve, offers substantial advantages. Among the advantages are reduced measurement noise and improved sensitivity. The method controls for mechanical and optical instabilities by providing a result based on relative differences rather than an absolute change. Therefore, an overall increase or decrease in the intensity of the light provided to the waveguides should not introduce corresponding errors into the results. Enhanced sensitivity is achieved by sampling SPR curves at more than one point such that shifts in the curves are more readily detected. As shown in FIG. 3, the SPR curve can be sampled at a number of different points (A–E). Sampling at any two of these points affords better detection of shifts in the curve than if merely one point is sampled. For example, if merely point D were sampled, a shift of the curve to the right could lead to sampling at point C, which would show no difference in the transmitted light intensity. By sampling at points C and D originally, a similar shift of the curve would be readily detected. Sampling at multiple points also enables selection of good sets, e.g., pairs for taking measurements. Good sets involve sampling at two or more points such that a shift of the SPR response curve causes the intensity of the light transmitted to increase for one member of the set and decrease for the other member(s) of the set. These opposing changes in the transmitted light intensity reveal that the sampling points lie on opposite sides of the resonance point in the SPR response curve.

This sampling at different points can be implemented by varying either the light propagation velocities within the waveguides or the wavelengths of the light beams. To obtain a result for any two light beams, the light beams can have different wavelengths and be directed through waveguides having the same light propagation velocities or through a single waveguide. Thus, where different wavelengths are used, there can be a one-to-one relationship between waveguides and types of ligands. Alternatively, the light beams can have the same wavelength and be directed through two or more waveguides having different light propagation velocities. The light propagation velocity can be varied by, e.g., using waveguides with different widths (FIG. 2) or varying the thickness of the second material (FIG. 1). In the embodiment using waveguides having different light propagation velocities, a set of at least two waveguides is required (see FIG. 4 for a detection device with four waveguides in a set) for each type of ligand.

While differential detection provides the primary improvement in sensitivity, sensitivity is also a function of the slope of the SPR response curve, since a steeper curve amplifies the effect of analyte binding on the change in intensity. The slope of the curve increases with increasing coverage of the optical waveguides with the metallic film. Therefore, increasing the length of the metallic film covering the waveguides affords the ability to achieve greater signal amplification. Since increasing the slope of the SPR response curve decreases the range of sampling points that are sensitive to shifts in the curve, using a greater number of sampling points increases the probability that measurement points will lie on the sloped region of the curve, where detection is more sensitive.

These new differential methods of SPR detection can be used to detect the presence of different analytes by using a number of waveguides. FIG. 4 shows a detection device suitable for multi-analyte detection using multiple types of ligands. In addition, by obtaining results at multiple times after the first time either continuously or at intervals, the new methods permit time-dependent analysis of ligand-analyte binding. These time-dependent results can be used to analyze binding kinetics.

Figure 5:
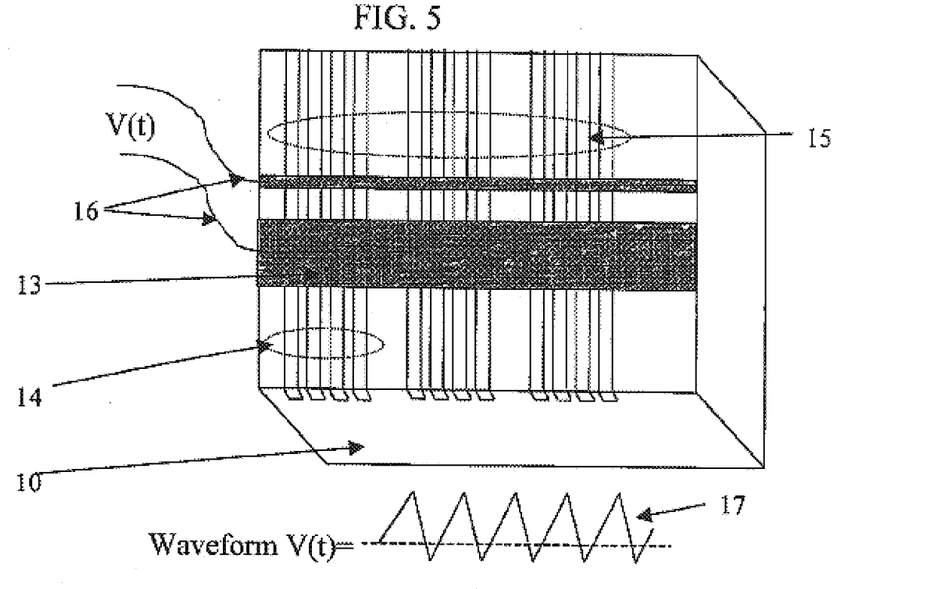
FIG. 5 is a diagram of a device for detection using multiple ligands adapted to provide an electric field.

The new methods also include use of an electric field with alternating polarity to decrease detection time and nonspecific binding of charged analytes. By applying an alternating electric field to samples containing charged analytes, binding can be enhanced during part of the cycle and inhibited when the polarity reverses. FIG. 5 shows an example of how the electric current can be provided using wires 16 to provide an electric field within the cell. In this configuration, the metallic film 13 with the ligands on its surface is being used as one of the conductive pads. Other embodiments can be made in which the electric field is provided by conductive pads that are separate from the metallic film having the ligands. Where the magnitude of the electric field in the sample is less than the strength of the analyte-ligand bond, binding of the analytes can be enhanced. In addition, the electric field can be applied using an asymmetric waveform 17, where the amplitude during the part of the cycle that enhances binding is greater than the amplitude during the part of the cycle that inhibits binding. Use of this asymmetric electric field can improve binding kinetics dramatically by using a field strength greater than the ligand-analyte binding strength during the binding phase to enhance binding, while applying a field having reduced strength during the inhibiting phase that is strong enough to overcome the binding strength of nonspecifically bound analytes (and thus remove these analytes), but not strong enough to disrupt specific ligand-analyte interactions. These methods improve the specificity and sensitivity of the detection devices.

General System

Figure 6:
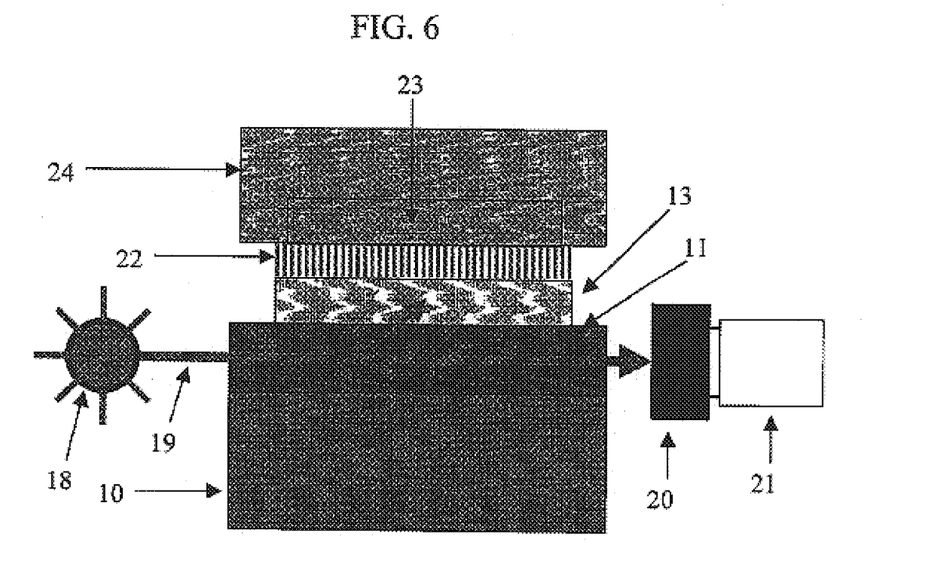
FIG. 6 is a diagram of a cross-section of a system using a detection device, illustrating its general operation for a particular waveguide.

The present invention also includes a system for SPR detection using the new detection devices and methods. FIG. 6 shows a diagram of a cross-section of a system using the detection device illustrating its general operation for a particular waveguide. A light source 18 transmits light 19 into a waveguide 11 using standard coupling methods, e.g., end-fire coupling, surface corrugations, or coupled waveguides. The light source 18 can be a laser, i.e., semiconductor laser, or laser diode. Where different wavelengths of light are used, there can be more than one light source 18 to transmit light into a particular waveguide. The light 19 that is transmitted through the waveguide is received by a photodetector 20, such as a charge-coupled device (CCD) which converts the intensity of the transmitted light into an electrical signal that can be digitized. If more than one wavelength of light is used, the different light beams can be separated by either optical separation techniques (e.g., filters or gratings) or electrical time or frequency multiplexing (e.g., modulating the different sources with different frequencies or time orthogonal signals).

The signal produced by the photodetectors are analyzed by a processor 21, which can include a differential amplifier, and/or, e.g., a handheld, personal, mobile or mainframe computer. The processor can use software to convert the signals into measured intensities. The measured intensities for sets of light beams are then processed in a calculation to provide a first calculated difference at a first time. At a second time sometime later, a second calculated difference between the sets of light beams is computed. The processor 21 compares the first calculated difference to the second calculated to indicate any shift of the SPR curve. The processor can provide results to a remote location via a data transmission system, e.g., fiber optic cable, the Internet, radiofrequency broadcast, or satellite. Conversely, the data transmission system can be used to provide electrical signals to a processor that performs calculations at a location that is remote from the detection device or system. By repeatedly performing (either continuously or at intervals) the steps computing a second calculated difference and comparing it to the first calculated difference, processor 21 can provide a series of time-dependent results. Time-dependent results are particularly useful to study kinetics.

The results provided by the processor are measures of analyte-ligand binding due to shifting of SPR curves. The ligand layer 22 is in contact with a sample, e.g., a liquid or gas, such air, containing the analytes 23 contained within a cell or conduit of a cell 24. The cell and the conduits of the cell can use known microfluidic techniques, see, e.g., U.S. Pat. No. 6,007,690. As analytes 23 in the sample bind to the ligand layer 22, the SPR curve for the waveguide shifts due to a change in the index of refraction of the metallic film. This shift changes the quantity of light that enters a SPW in the metallic film 13. Consequently, analyte-ligand binding affects the amount of light transmitted to the photodetector so that the processor can provide results that measure analyte binding.

In one embodiment, the new system features detection based on computing differences in intensities for sets of light beams. These sets of light beams can be light beams having different wavelengths, in which case they can be transmitted through the same waveguide, or light beams transmitted through waveguides having different light propagation velocities. The propagation velocity of the waveguides can be varied, i.e., by varying their physical parameters (e.g. width) or the thickness of the second material.

Figure 7:
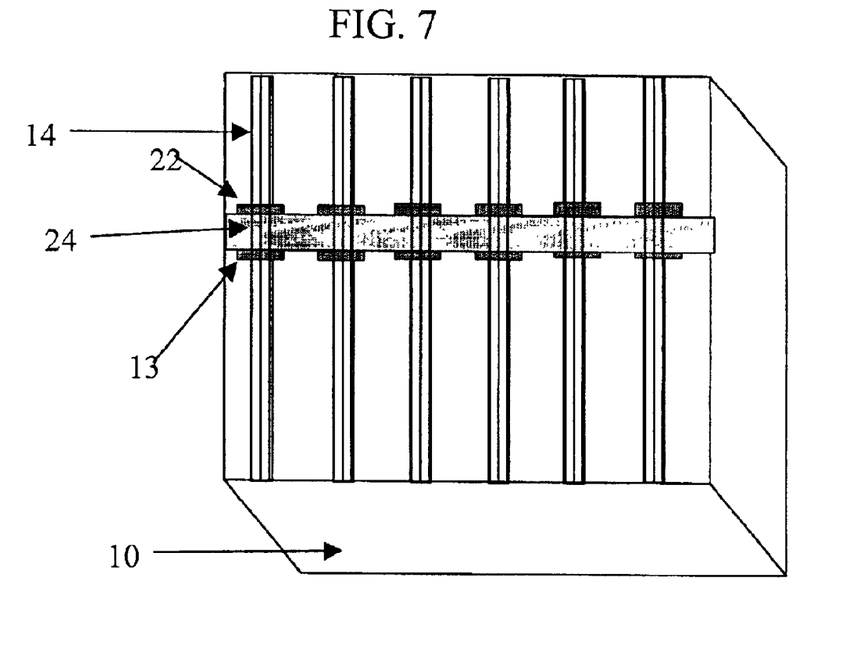
FIG. 7 is a diagram of a single conduit transversing a device for detection using multiple ligands.
Figure 8:
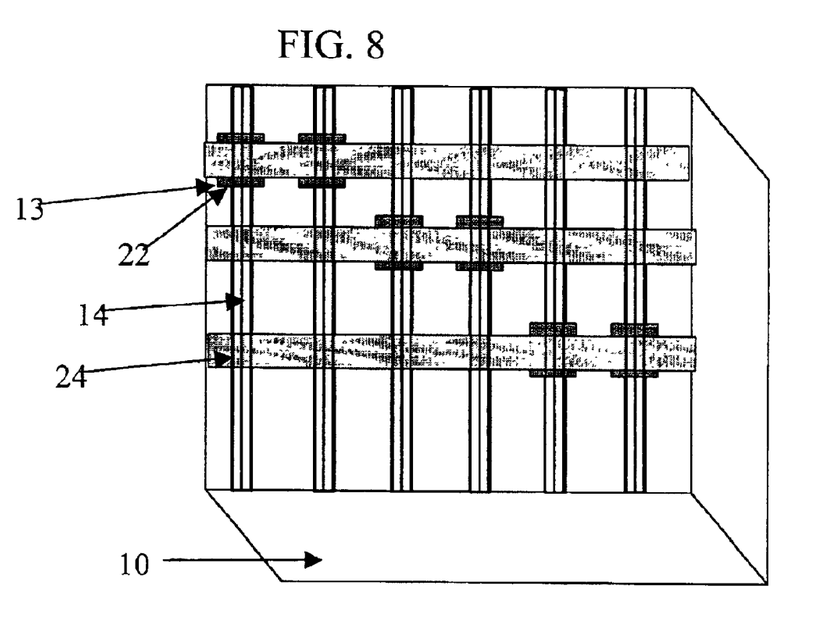
FIG. 8 is a diagram of multiple conduits transversing a device for detection using multiple samples and multiple ligands.

Using the new system, one can perform multi-analyte and multi-sample differential SPR detection. FIG. 7 shows a detection device that can be used in a system for multi-analyte detection, since each set of waveguides 14 can be used to measure a particular ligand-analyte binding interaction. The sample containing the analytes is provided to the ligand layers 22 on the metallic pads 13 of the detection device by conduit 24. FIG. 8 diagrams a detection device suitable for multi-sample detection using multiple ligands. The detection device of FIG. 8 differs from that in FIG. 7 because it has multiple conduits 24 capable of supplying multiple samples, each containing analytes. Using these detection devices in the new system requires a photodetection system for multiple light spots to detect the light beams from the array of waveguides, and the light beams can be provided either from a single light source or multiple sources.

The system can also include a voltage source, e.g., a power supply (i.e., a Hewlett-Packard signal generator). This power supply is used to provide current through wires to physically separated conductive pads, as shown in FIG. 5. The current can be supplied by the source such that the field strength is less than the binding strength between the ligand layer and the analytes. Using this approach, the electric field enhances binding during part of its cycle and inhibits binding and enhances disruption of nonspecific binding during the other part of the cycle. An asymmetric electric field can also be used. This asymmetric field has lower amplitude during the part of the cycle where polarity is reversed to inhibit binding and a greater amplitude during the part of the cycle that enhances binding. The strength of the electric field created during the portion of the cycle that enhances binding can exceed the ligand-analyte binding strength. A wire from the power supply can be connected to a metal pad having a ligand layer or the conductive pads can be distinct from those containing the ligand layers.

APPLICATIONS

There are many applications for the new devices, systems, and methods for differential SPR detection. They offer many advantages in a variety of settings ranging from the laboratory to the field.

In a clinical setting, ease of use, efficiency, and low cost are important benefits. The new differential SPR detection systems are inexpensive and easy for laboratory technicians to use. The systems can be entirely automated and merely require providing a sample to the system to conduct analysis. Since the ligand layers can be used to detect a wide variety of compounds, laboratory use can range from genetic testing using patient DNA, which can be extracted from white blood cells, to standard analysis of body fluids, e.g., blood, urine, or sputum for, e.g., pathogens or drugs. The detection devices can be generic disposable bundles of waveguides with metallic films that are modified with ligands within the detection systems prior to analysis using, e.g., a mechanical spotting robot or an ink-jet based spotting device (e, g., Packard BioScience and Canon). Sample preparation can be conducted within the system using automated devices (e.g., Aclara and Caliper). In addition, the samples for analysis can be collected in bar coded containers that the systems read in conjunction with the analysis. Using this approach, the possibility of contamination or misidentification is greatly reduced. These advantages can be achieved while conducting highly efficient analysis. By using detection devices with multiple ligand layers and a system that uses multiple conduits to provide different samples, a number of samples can be simultaneously analyzed for the presence of a number of different analytes. Thus, the system can perform blood analyses and urinalyses for many, e.g., 50 or more, patients in parallel for many, e.g., 50 or more, analytes.

These systems are also user-friendly, merely requiring the laboratory technician to provide the samples for analysis and await results. To further streamline the process, the results can be directly fed into a computer network in the laboratory, e.g., via a serial port interface, and placed in a file that can be provided to the treating physician and patient by, e.g., an email. Thus, the ability to link the results of this SPR detection scheme into a computer system and/or a communications network, e.g., a local area network (LAN), an intranet, or the Internet, reduces communication time and the probability of errors in recording results or communicating them.

The benefits of the new differential SPR detection devices, methods, and systems extend beyond the laboratory setting. The systems can be used at home or in doctor's offices to conduct rapid analyses and share the results with remote locations. Consequently, these systems permit doctors to increase the accuracy of diagnosis and prescribe treatments more quickly. For patients, applications of SPR detection systems include monitoring blood glucose levels by diabetic patients and pathogen testing by individuals with compromised immune systems. These systems can provide the patient with results, e.g., using an integrated processor or by output to a handheld computer, and send these results to the patient's doctor via wireless transmission, the Internet, or telephone lines. One adaptation of these systems can include an alarm feature activated if the glucose level passes a certain pre-determined level. These SPR detection systems can be portable, since the detection devices can be microfabricated and the light sources and photodetectors can be integrated in a solid-state architecture for providing electrical signals to a microprocessor.

Similarly, the advantages of these differential SPR detection systems make them suitable for use in the field. Their portability and sensitivity permit these systems to provide accurate results at any location. Since the detection devices can be small, light, and inexpensive, these SPR devices are also ideal for performing a number of analyses without need to re-supply. For example, these systems can be used by hydrologists to detect water contamination or by military personnel to monitor continuously for the presence of biological or chemical weapons. Another application is the detection of viral infections in shrimps; an outbreak of such infection can kill off an entire shrimp crop in an aquaculture farm, if not detected within hours. These systems can perform analyses for a number of different analytes simultaneously and can be configured to transmit the results automatically back to an office or outpost. Thus, the monitoring personnel need not remain present at the location being monitored. The system can be configured to change detection devices automatically such that many devices can be sampled before manual intervention is required.

EXAMPLE

The invention is further described in the following example, which does not limit the scope of the invention described in the claims.

A detection device was fabricated on a chip using a borosilicate glass substrate having dimensions of 1 cm by 2 cm. Waveguides with a width and depth of 6 microns were formed along the length of the chip by a standard ion exchange process that replaces sodium with potassium in the substrate. The chip included seven waveguides spaced apart by 100 microns and formed in straight parallel lines. A gold pad with a thickness of 3 microns was deposited over all waveguides using electron beam deposition and a photoresist.

An experiment was perform to confirm the viability of the chip for use in SPR detection. In the experiment, a single semiconductor laser provided light having a wavelength of 0.633 microns at 2 mW of power. A cylindrical lens having a focal length of 0.5 cm formed a focused light line in the plane of the waveguides and was used to couple light from this laser into all waveguides simultaneously. The light beams coupled into the waveguides were successfully transmitted through them, passing underneath the gold pads. Samples of sugar water of varying concentration were flowed over the waveguides to measure the index of refraction of these samples, which varies as a function of the sugar concentration. The light transmitted through the waveguides was detected using a CCD camera that formed an image of seven light dots, each corresponding to a light beam transmitted through the waveguides. The intensity of the transmitted light was measured with an oscilloscope, which was connected to the CCD camera.

The experiment demonstrated the ability to use this detection device in SPR detection. As the sugar sample concentration increased, the measured light intensity traced a typical SPR curve. When a sugar water concentration created an index of refraction such that the phase velocity of the evanescent field matched that of the plasmon wave in the gold, the light transmitted through the waveguides dropped sharply. Thus, the resonance point for the SPW in the gold was observed.

The detection device used in this experiment is modified to vary the propagation parameters of the waveguides by creating waveguides having distinct widths in the ion exchange process. In addition, a ligand layer is deposited using 0.1 M samples of thiols using microstamping as described in U.S. Pat. No. 5,512,131. The detection device used in the experiment and variations on that device is then used in differential detection by subtracting signals obtained by the photodetection apparatus for a two light beams having different light propagation velocities in the detection device at one time and comparing that difference to one taken for that pair at another time. The light propagation velocities are varied by using semiconductor lasers that provide different wavelengths of light to the detection device.

OTHER EMBODIMENTS

A number of embodiments of the invention have been described. Nevertheless, it will be understood that various modifications can be made without departing from the spirit and scope of the invention. For example, a multi-sample detection system with a single ligand layer can use the new methods for differential SPR detection. Accordingly, other embodiments are within the scope of the following claims.

What is claimed is:

1. A detection system, comprising:
    (a) a cell directing at least one sample to a metallic film that supports a surface plasmon wave and covers at least a portion of at least one waveguide;
    (b) a light source that transmits light beams into the waveguides;
    (c) a detector to convert the transmitted light into an electrical signal;
    (d) a processor that performs the steps of
        converting the electrical signals into measured intensities;
        computing a first calculated difference between measured intensities for two light beams at a first time, wherein the two light beams each have a distinct light propagation velocity within the waveguides;
        computing a second calculated difference between measured intensities for the two light beams at a second time later than the first time; and
        comparing the first calculated difference to the second calculated difference, wherein a difference between the first calculated difference and the second calculated difference indicates a shift of the surface plasmon resonance curve.

2. The system of claim 1, wherein ligand layers for binding analytes are attached to the metallic films.

3. The system of claim 2, further comprising:
    (e) a voltage source connected through wires to physically separated conductive pads within the cell to provide an electric field across a separation, wherein the electric field has a field strength less than a binding energy between a ligand in the ligand layer and an analyte.

4. The system of claim 2, further comprising:
    (e) a voltage source connected through wires to physically separated conductive pads within the cell to provide an alternating polarity electric field across a separation, wherein the electric field has a cycle, wherein the polarity during a first portion of the cycle is opposite to the polarity during a second portion of the cycle, and wherein the electric field has a greater strength during the first portion of the cycle that causes binding of the analytes than the strength during the second portion of the cycle that causes unbinding of the analytes.

5. The system of claim 3 or 4, wherein the conductive pads comprise the metallic film.

6. The system of claim 1, wherein the light source is a laser or light emitting diode.

7. The system of claim 1, wherein the light source is a semiconductor laser.

8. The system of claim 1, wherein the detector is a photodetector or charge-coupled device.

9. The system of claim 1, wherein the two light beams comprise light beams having different wavelengths.

10. The system of claim 1, wherein the two light beams are transmitted through the same waveguide.

11. The system of claim 1, wherein the two light beams are transmitted through two waveguides, each having a distinct light propagation velocity.

12. The system of claim 1, wherein the two light beams are transmitted through two waveguides, each having a distinct shape or size.

13. The system of claim 1, wherein the cell includes one or more conduits to flow the sample over the ligand layers.

14. The system of claim 1, wherein the processor continuously or at intervals repeats the steps of computing a second calculated difference between measured intensities for the two light beams at a second time later than the first time; and comparing the first calculated difference to the second calculated difference, wherein a difference between the first calculated difference and the second calculated difference indicates a shift of the surface plasmon resonance curve.

15. The system of claim 1, wherein the electrical signals are digital signals.

16. The system of claim 1, wherein the processor comprises a differential amplifier, or a handheld, mobile, personal, or mainframe computer.

17. The system of claim 1, wherein the difference between the first calculated difference and the second calculated difference is provided by satellite, radiofrequency broadcast, fiber optic cable, or electric wire to a location physically separated from the light sources and detectors.

18. A method of detecting a shift of a surface plasmon resonance curve, the method comprising:

(a) transmitting a plurality of light beams through at least one waveguide on a detection device, wherein the detection device comprises
at least one metallic film, wherein each of the metallic films covers at least a portion of each of the waveguides and supports a surface plasmon wave;

(b) measuring the intensity of a plurality of light beams transmitted through the waveguides;

(c) computing a difference between the measured intensity of any two of the beams, wherein the light beams in the pair each have a distinct light propagation velocity within the waveguides, to provide a first calculated difference for the two beams at a first time;

(d) providing at least one sample to the metallic film;

(e) computing a difference between the intensity of the two light beams to provide a second calculated difference for the two beams at a second time; and (f) comparing the first calculated difference to the second calculated difference, wherein a difference between the first calculated difference and the second calculated difference indicates a shift of the surface plasmon resonance curve.

19. The method of claim 18, further comprising repeating steps e) and f) continuously or at intervals.

20. The method of claim 18, wherein the detection device further comprises ligand layers for binding analytes on the metallic films.

21. The method of claim 20, further comprising providing an alternating polarity electric field to the sample, wherein the electric field has a field strength less than a binding strength between a ligand in the ligand layer and an analyte.

22. The method of claim 20, further comprising providing an alternating polarity electric field, to the sample having a cycle, wherein the polarity during a first portion of the cycle is opposite to the polarity during a second portion of the cycle, and wherein the electric field has a greater strength during the first portion of the cycle that causes binding of the analytes than the strength during the second portion of the cycle that causes unbinding of the analytes.

23. The method of claim 18, wherein the light beams comprise different wavelengths.

24. The method of claim 18, wherein two light beams are transmitted through the same waveguide.

25. The method of claim 18, wherein the two light beams are transmitted through two waveguides, each having a distinct light propagation velocity.

26. The method of claim 18, wherein the two light beams are transmitted through two waveguides, each having a distinct shape or size.

27. The method of claim 18, wherein the detection device comprises waveguides on a substrate, wherein the substrate comprises a first material having a surface, wherein the surface is covered by a second material having an index of refraction lower than the index of refraction of the first material.

28. The method of claim 27, wherein the two light beams are transmitted through two waveguides, each covered by a distinct thickness of the second material.

* * * * *